(12) United States Patent
Ling et al.

(10) Patent No.: US 9,179,532 B2
(45) Date of Patent: Nov. 3, 2015

(54) CROSS ARM OF X-RAY EQUIPMENT AND A CORRESPONDING X-RAY EQUIPMENT

(71) Applicant: GE MEDICAL SYSTEMS GLOBAL TECHNOLOGY COMPANY LLC, Waukesha, WI (US)

(72) Inventors: Zhenggang Ling, Beijing (CN); Zhengjun Wang, Beijing (CN); Yicheng Wang, Beijing (CN); Yong Xu, Beijing (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 106 days.

(21) Appl. No.: 13/929,275

(22) Filed: Jun. 27, 2013

(65) Prior Publication Data

US 2014/0003584 A1   Jan. 2, 2014

(30) Foreign Application Priority Data

Jun. 29, 2012   (CN) .......................... 2012 1 0220523

(51) Int. Cl.
*A61B 6/00* (2006.01)
*H05G 1/02* (2006.01)

(52) U.S. Cl.
CPC ................ *H05G 1/02* (2013.01); *A61B 6/4441* (2013.01); *A61B 6/4452* (2013.01); *A61B 6/4476* (2013.01)

(58) Field of Classification Search
CPC ...... A61B 6/44; A61B 6/4429; A61B 6/4452; A61B 6/4476; A61B 6/4482; A61B 6/447; G01N 2223/308
See application file for complete search history.

(56) References Cited

U.S. PATENT DOCUMENTS

| | | | |
|---|---|---|---|
| 3,892,967 A * | 7/1975 | Howarth et al. | 378/197 |
| 4,412,346 A * | 10/1983 | Takenouti et al. | 378/181 |
| 4,651,007 A * | 3/1987 | Perusek et al. | 250/363.08 |
| 4,964,151 A * | 10/1990 | Trotel | 378/198 |
| 7,753,585 B2 * | 7/2010 | Laupper | 378/197 |
| 2012/0114098 A1* | 5/2012 | Mikami et al. | 378/62 |
| 2014/0003584 A1* | 1/2014 | Ling et al. | 378/197 |
| 2014/0003585 A1* | 1/2014 | Ling et al. | 378/197 |

* cited by examiner

*Primary Examiner* — Thomas R Artman
(74) *Attorney, Agent, or Firm* — GE Global Patent Operation; Marc A. Vivenzio

(57) ABSTRACT

A cross arm for X-ray equipment. The cross arm comprises a guide on the cross arm, a tube on the guide, and a linkage device, wherein the tube is configured to move along the guide when the cross arm rotates.

18 Claims, 3 Drawing Sheets

CROSS ARM OF X-RAY EQUIPMENT AND A CORRESPONDING X-RAY EQUIPMENT

TECHNICAL FIELD

Embodiments of the present invention relate to medical imaging devices, and in particular, to X-ray equipment.

BACKGROUND OF THE INVENTION

In order to be adaptive to different filming positions, a cross arm 101 of a medical X-ray equipment is designed to rotate about a center shaft, i.e., to rotate on a plane that is vertical to the floor where the X-ray equipment is located. The most frequently used filming positions are chest position and decubitus position. When the chest position is to be taken, the cross arm 101 is at a horizontal position, and a tube 103 needs to be moved along a guide 102 on the cross arm to the farthest end, i.e., the distance from the tube 103 to a detector 104 (SID) is adjusted to maximum; when the decubitus position is to be taken, the cross arm is at a vertical position, the tube 103 needs to be moved along the guide 102 on the cross arm to the nearest end, i.e., the distance from the tube 103 to the detector 104 (SID) is adjusted to minimum, as shown in FIGS. 1A and 1B.

As for an existing manually-operated cross arm, a doctor needs to complete the above operation via the following two steps: first move a tube, adjust SID, and then rotate a cross arm. If the cross arm is rotated from a horizontal position to a vertical position first of all, SID cannot be adjusted for the reason that the position of the tube is too high.

BRIEF SUMMARY OF THE INVENTION

Embodiments of the present invention provide a novel cross arm of X-ray equipment and a corresponding X-ray equipment, so as to complete adjustment of SID while rotating the cross arm, thereby solving the problem that filming different positions in the prior art needs step-by-step operation.

Embodiments of the present invention provide a cross arm of X-ray equipment, comprising a guide provided on the cross arm and a tube provided on the guide, characterized in that, the cross arm further comprising a linkage device, such that the tube can be impelled to move along the guide when the cross arm rotates.

Embodiments of the present invention provide a cross arm of X-ray equipment, wherein the linkage device further comprises a cross arm rotating means, configured to rotate the cross arm; a rotation actuating/braking means, configured to allow or disallow the rotation of the cross arm, and a tube towing means, configured to allow the tube to move along the guide. The linkage device may further comprise a rotary force driving means, configured to transmit a power generated by rotation of the cross arm to the tube towing means, and a rotary force clutch means, configured to interrupt or transmit the power that is transmitted by the rotary force driving means to the tube towing means.

Embodiments of the present invention provide a cross arm of X-ray equipment, wherein the cross arm rotating means comprises a rotary shaft and a rotary gear capable of rotating about the rotary shaft.

Embodiments of the present invention provide a cross arm of X-ray equipment, wherein the rotary gear is fixedly provided on the cross arm.

Embodiments of the present invention provide a cross arm of X-ray equipment, wherein the rotation actuating/braking means comprises a brake and a braking gear that is provided on a shaft core of the brake, the braking gear and the rotary gear being engaged with each other.

Embodiments of the present invention provide a cross arm of X-ray equipment, wherein the rotary force driving means comprises a driving sprocket provided on the shaft core of the brake and a driving chain engaged with the driving sprocket.

Embodiments of the present invention provide a cross arm of X-ray equipment, wherein the shaft core of the brake can rotate and impel the braking gear and the driving sprocket to rotate together when the brake is energized, and can remain immovable when the brake is de-energized.

Embodiments of the present invention provide a cross arm of X-ray equipment, wherein the rotary force clutch means comprises a clutch and a clutch sprocket provided on a clutch shaft core, the clutch sprocket and the driving chain being engaged with each other.

Embodiments of the present invention provide a cross arm of X-ray equipment, wherein the clutch comprises a sucker and an armature that are fixedly connected with the clutch shaft core, wherein the sucker sucks the clutch sprocket tightly via the armature when the clutch is energized, such that the clutch sprocket can impel the clutch shaft core to rotate. In an embodiment, the sucker does not work when the clutch is de-energized, such that the clutch sprocket can freely rotate about the clutch shaft core.

Embodiments of the present invention provide a cross arm of X-ray equipment, wherein the tube towing means comprises a tube towing wheel provided on the clutch shaft core, a tube towing chain engaged with the tube towing wheel, a shaft fixed on the cross arm, a SID brake provided on the shaft and a sprocket that rotates about the shaft and is engaged with the tube towing chain.

Embodiments of the present invention provide a cross arm of X-ray equipment, wherein the tube towing means further comprises an encoder for measuring rotation degrees of the tube towing wheel, wherein output results of the encoder are fed back to a control console of X-ray equipment, and when the rotation degrees of the tube towing wheel reach a degree that is predefined by an operator, the control console of X-ray equipment will control the clutch and the SID brake to cut a power.

Embodiments of the present invention provide a cross arm of X-ray equipment, wherein the cross arm further comprises at least one photoelectric sensor provided at the moving path of the tube, capable of feeding back to the control console of X-ray equipment a message that the tube arrives at the position where the sensor is located.

Embodiments of the present invention further provide an X-ray equipment, comprising the cross arm of X-ray equipment according to embodiments of the present invention. According to an embodiment of the present invention, the X-ray equipment comprises a cross arm. According to an embodiment of the present invention, the cross arm comprises a guide on the cross arm, a tube on the guide, and a linkage device, wherein the tube is configured to move along the guide when the cross arm rotates.

The cross arm of X-ray equipment and the corresponding X-ray equipment, as provided by embodiments of the present invention, have the technical effect of allowing the tube and the cross arm to move together when the cross arm rotates. This reduces operation steps and improves the maneuverability and convenience of X-ray equipment In accordance with embodiments of the present invention, adjustment of SID can be completed automatically without being towed by a motor, thereby reducing the cost of equipment and improving market competitiveness.

DETAILED DESCRIPTION OF THE INVENTION

Embodiments of the present invention are further described below with reference to the drawings and the embodiments.

Figure 1A:
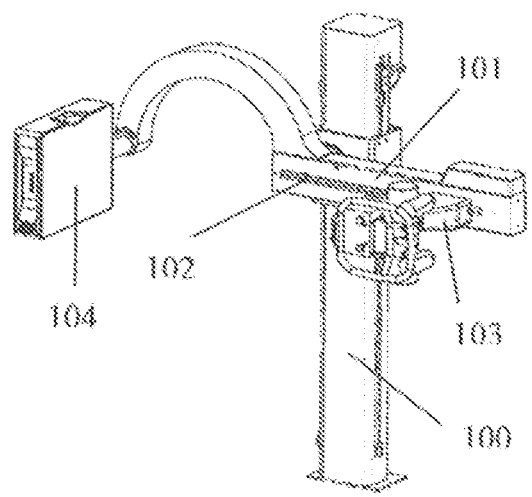
FIG. 1A is a schematic diagram of positions of a cross arm and a tube when a chest position is taken by a medical X-ray equipment.
Figure 1B:
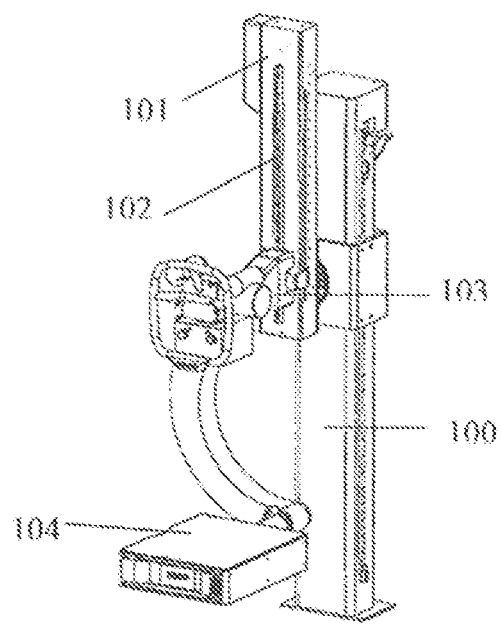
FIG. 1B is a schematic diagram of positions of a cross arm and a tube when a decubitus position is taken by a medical X-ray equipment.
Figure 2A:
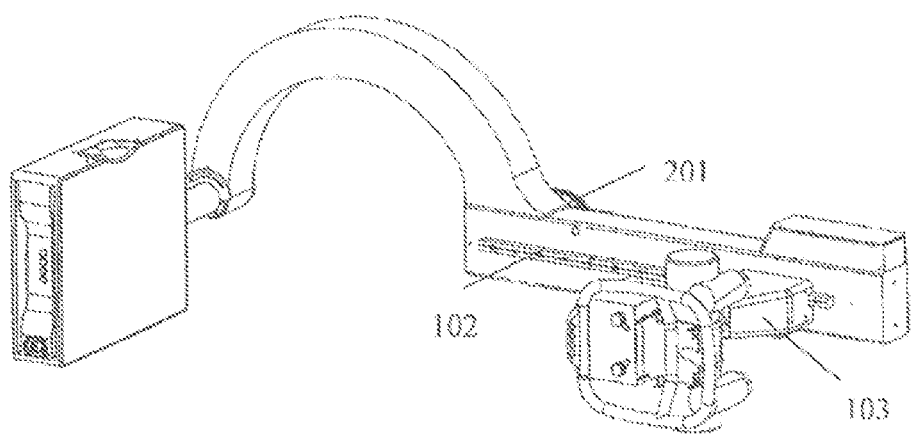
FIG. 2A is a front view of an overall structure of the cross arm of X-ray equipment in accordance with an embodiment of the present invention.
Figure 2B:
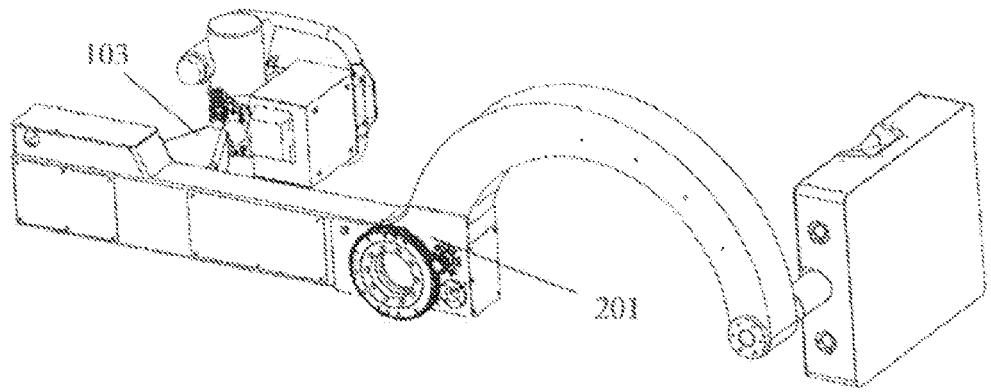
FIG. 2B is a rear view of an overall structure of the cross arm of X-ray equipment in accordance with an embodiment of the present invention.

FIG. 2 is a schematic diagram of an overall structure of the cross arm of X-ray equipment as provided by an embodiment of the present invention. FIG. 2A shows the structure of the cross arm that is seen from the front, i.e., the direction of watching when an X-ray equipment operator conducts operation and control. FIG. 2B shows the structure of the cross arm that is seen from the rear, i.e., the direction opposite to the direction of watching when the X-ray equipment operator conducts operation and control, comprising a guide 102 provided on the cross arm, a tube 103 capable of moving along the guide 102 and a linkage device 201, In accordance with an embodiment of the present invention, when the operator rotates the cross arm, i.e., rotates the cross arm on a plane that is vertical to the floor where the X-ray equipment is placed, the linkage device 201 can transmit the power of rotating to the tube 103, so as to enable the tube 103 to move along the guide 102. When the cross arm is rotating, the tube can move with the cross arm, thereby reducing operation steps and improving maneuverability and convenience of equipment. Moreover, adjustment of SID can be completed automatically without being towed by a motor, thereby reducing equipment's costs and improving market competitiveness.

Figure 3A:
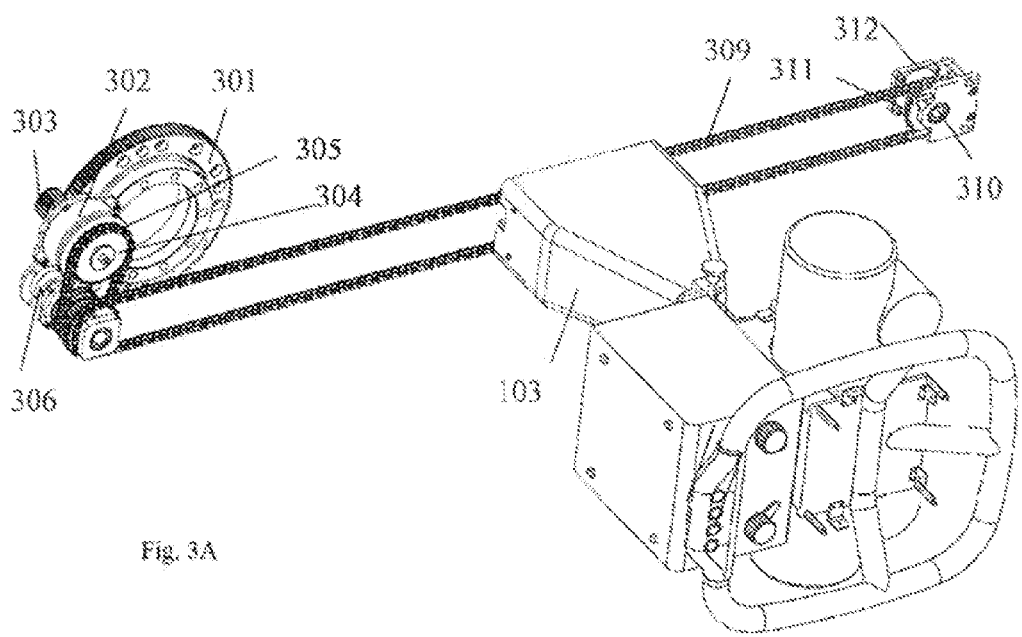
FIG. 3A is a front view of the linkage device in accordance with an embodiment of the present invention.
Figure 3B:
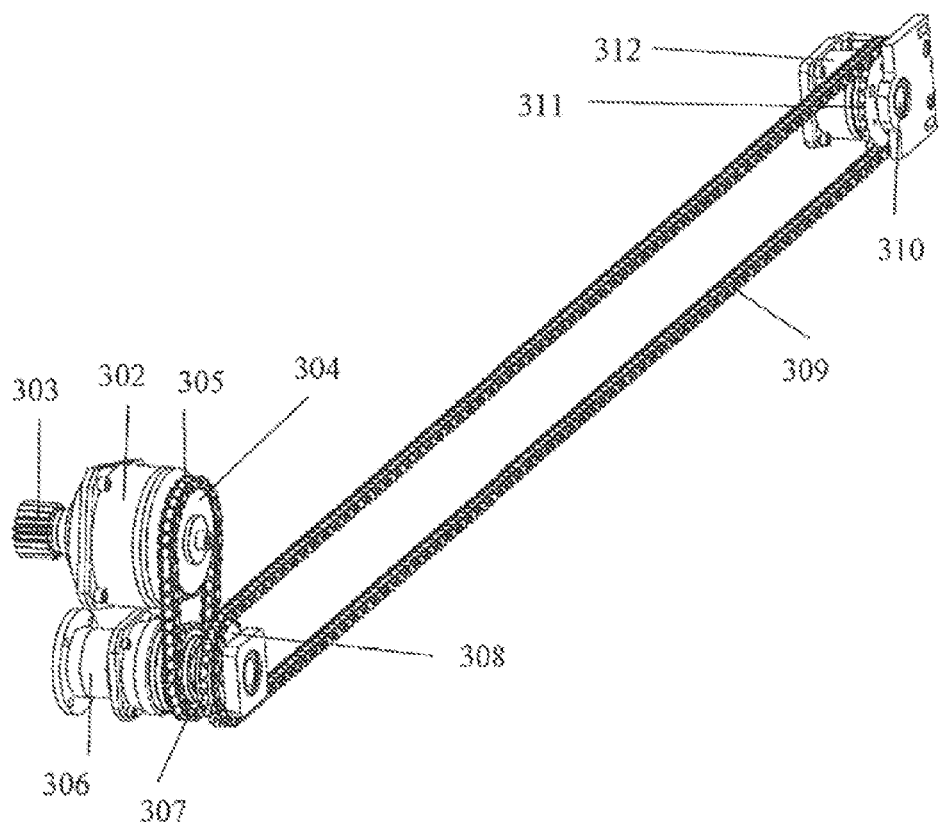
FIG. 3B is a side view of the linkage device in accordance with an embodiment of the present invention.
Figure 3C:
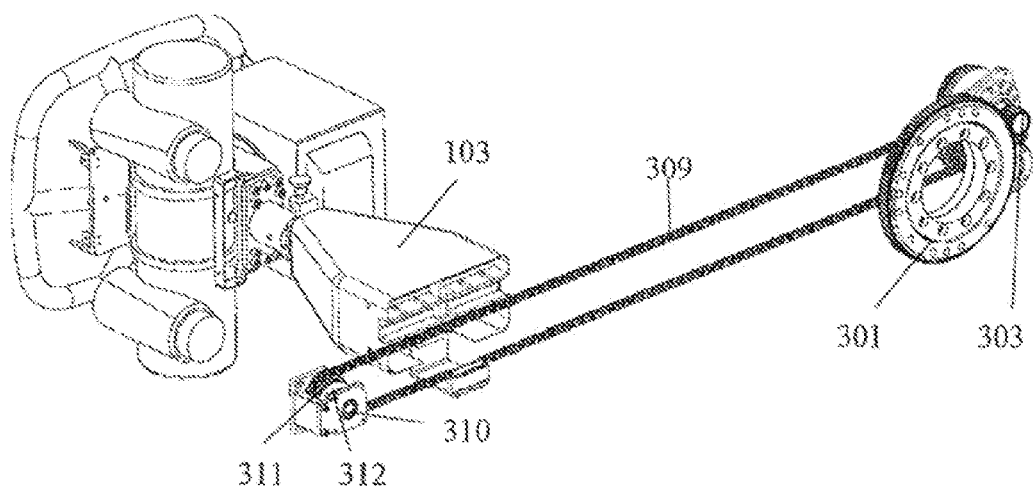
FIG. 3C is a rear view of the linkage device in accordance with an embodiment of the present invention.

FIG. 3 shows the specific structure of the linkage device 201 in accordance with an embodiment of the present invention, wherein FIG. 3A is a front view, i.e., a schematic diagram that is seen from the direction of watching when the X-ray operator conducts operation and control, FIG. 3B is a side view, and FIG. 3C is a rear view. In at least one embodiment, the linkage device 201 is wrapped the housing of the cross arm, so FIG. 3 omits the housing of the cross arm and the guide 102 thereon in order to clearly show the structure of the linkage device 201.

As seen from FIG. 3, the linkage device 201 may comprises a rotary gear 301 for rotation of the cross arm, wherein the rotary gear is capable of rotating about a shaft that is fixed on a vertical post 100 of X-ray equipment relative to the cross arm. The linkage device 201 further comprises a brake 302, a braking gear 303 fixedly provided on a shaft core of the brake 302 and a driving sprocket 304 The linkage device 301 further comprises a clutch 306, a clutch sprocket 307 provided on a shaft core of the clutch and a tube towing wheel 308 fixedly provided on the shaft core of the clutch. In accordance with an embodiment of the present invention, the linkage shaft 201 may further comprise a shaft 310 fixed on the cross arm, a SID brake 312 provided on the shaft and a sprocket 311 capable of rotating about the shaft 310, In accordance with an embodiment of the present invention, the rotary gear 301 is engaged with the braking gear 303, the driving sprocket 304 and the clutch sprocket 307 are engaged with a driving chain 305 respectively, and the tube towing wheel 308 and the sprocket 311 are engaged with a tube towing chain 309 respectively.

In accordance with an embodiment of the present invention, when the clutch 306 is energized, a sucker in the clutch combines the clutch sprocket 307 and the clutch shaft core tightly via an armature. In accordance with an embodiment of the present invention, when the clutch 306 is de-energized, the clutch sprocket 307 freely rotates about the clutch shaft core. When the clutch is de-energized, the sucker does not work.

In accordance with an embodiment of the present invention, when a user needs to rotate the cross arm and adjust SID, the user only needs to energize the brake 302 and the clutch 306, and then manually rotate the cross arm so as to make it rotate about the rotating shaft of the cross arm, thereby impelling the rotary gear 301 provided on the rotating shaft to rotate. In accordance with an embodiment of the present invention, when the rotary gear 301 is engaged with the braking gear 303 and the brake 302 is in an energizing state, the braking gear 303 will also rotate, following the rotary gear 301, and impel the driving sprocket 304 to rotate together. In accordance with an embodiment of the present invention, when the driving sprocket 304 is engaged with the driving chain 305, impelled by the driving sprocket 304, the driving chain 305 starts transmitting the power generated by rotation to the clutch sprocket 307 which is also engaged with it. In accordance with an embodiment of the present invention, the clutch 306 can combine the clutch sprocket 307 and the clutch shaft core tightly when being energized; impelled by the driving chain 305, the clutch sprocket 307 will impel the clutch shaft core to rotate. In accordance with an embodiment of the present invention, the tube towing wheel 308 is always fixed relative to the clutch shaft core; the tube towing wheel 308 will also be impelled by the clutch shaft core to rotate, thereby further impelling the tube towing chain 309 to move. In accordance with an embodiment of the present invention, when the sprocket 311 is engaged with the tube towing chain 309, the sprocket 311 will also be impelled to rotate about the shaft 310. As shown in FIG. 3C, the tube towing chain 309 impels the tube 103 to move horizontally along the guide on the cross arm while moving horizontally along the cross arm.

When the user rotates the cross arm to an appropriate position, the system will automatically de-energize the brake 302 and put the SID brake 312 in a braking state. In accordance with an embodiment of the present invention, when the braking gear 303 cannot rotate, the rotary gear 301 cannot rotate either, the cross arm will be immovable, and the tube naturally has no power to move and can remain fixed.

In accordance with an embodiment of the present invention, if the user only wishes to rotate the cross arm while keeping SID unchanged, i.e., the tube is immovable, the system will only energize the brake 302 while de-energizing the clutch 306, and put the SID brake 312 in a braking state, so as to prevent the sprocket 311 from rotating. In accordance with an embodiment of the present invention, when the brake 302 is energized, the cross arm can rotate normally, but when the clutch 306 is de-energized, the clutch sprocket 307 will freely rotate about the clutch shaft core, the power generated by rotation will be unable to be transmitted via the clutch shaft core to the tube towing wheel 308, and moreover, the sprocket 311 cannot rotate, and the tube will remain immovable.

In accordance with an embodiment of the present invention, during the actual application of the medical X-ray equipment, SID is generally adjusted from 1800 mm to 1000 mm, or adjusted from 1000 mm to 1800 mm, and the moving distance of the tube is fixed. Moreover, the cross arm may also comprise two modes of rotating from horizontal to vertical or from vertical to horizontal. Hence, as long as such mechanical parameters as diameters of the rotary gear 301, braking gear 303, driving sprocket 304, clutch sprocket 307 and tube towing wheel 308 are properly calculated when the linkage device is designed, it can be guaranteed that when the cross arm moves to the horizontal or vertical position, the tube exactly moves a required distance.

According to an embodiment of the present invention, it the tube is to be enabled to move any distance, an encoder is needed to take participation, which encoder is used to measure an angle for which the tube towing wheel 308 has rotated, and to transmit the angle value to a control console. Since the rotating angle of the tube towing wheel 308 corresponds one by one to the moving distance of the tube, only according to the angle, the control console can judge whether the tube has moved to the position as preset by the user to which SID corresponds; if the preset position is reached, the control console will de-energize the clutch 306 and put the SID brake 312 in a breaking state, and the tube will remain immovable.

According to an embodiment of the present invention, on the cross arm, each frequently used position point of the tube to which SID corresponds, is provided with a photoelectric sensor; when the tube moves to the position point as preset by the user via the control console to which SID corresponds, the photoelectric sensor at this position point will sends a signal to the control console, the control console will de-energize the clutch 306 and put the SID brake 312 in a braking state after receiving the signal, and the tube will remain immovable.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A cross arm for X-ray equipment, the cross arm comprising:
   a guide on the cross arm;
   a tube configured to move along the guide when the cross arm rotates; and
   a linkage device comprising:
   a cross arm rotor configured to rotate the cross arm;
   a rotation actuator configured to allow and disallow the rotation of the cross arm;
   a tube towing mechanism configured to move the tube along the guide;
   a rotary force drive configured to transmit a power generated by the rotation of the cross arm to the tube towing mechanism; and
   a rotary force clutch configured to interrupt or to transmit the power transmitted by the rotary force drive to the tube towing mechanism.

2. The cross arm according to claim 1, wherein the cross arm rotor comprises a rotary shaft and a rotary gear configured to rotate about the rotary shaft.

3. The cross arm according to claim 2, wherein the rotary gear is fixed on the cross arm.

4. The cross arm according to claim 2, wherein the rotation actuator comprises:
   a brake; and
   a braking gear on a shaft core of the brake,
   wherein the braking gear and the rotary gear are engaged with each other.

5. The cross arm according to claim 4, wherein the rotary force driver comprises:
   a driving sprocket on the shaft core of the brake; and
   a driving chain engaged with the driving sprocket.

6. The cross arm according to claim 5, wherein the shaft core of the brake is configured to:
   rotate;
   drive the braking gear and the driving sprocket to rotate together when the brake is energized; and
   remain immovable when the brake is de-energized.

7. The cross arm according to claim 5, wherein the rotary force clutch comprises a:
   clutch; and
   clutch sprocket on a clutch shaft core,
   wherein the clutch sprocket and the driving chain are engaged with each other.

8. The cross arm according to claim 7, wherein the clutch comprises a sucker and an armature, wherein the sucker and the armature are fixedly connected with the clutch shaft core, wherein the sucker sucks the clutch sprocket tightly through the armature when the clutch is energized, such that the clutch sprocket drives the clutch shaft core to rotate and the sucker does not work when the clutch is de-energized, such that the clutch sprocket freely rotates about the clutch shaft core.

9. The cross arm according to claim 7, wherein the tube towing mechanism comprises:
   a tube towing wheel on the clutch shaft core;
   a tube towing chain engaged with the tube towing wheel;
   a tube towing shaft fixed on the cross arm;
   a SID brake provided on the tube towing shaft; and
   a sprocket configured to rotate about the tube towing shaft and is engaged with the tube towing chain.

10. The cross arm according to claim 9, wherein the tube towing mechanism further comprises an encoder configured to measure rotation degrees of the tube towing wheel, wherein output results of the encoder are fed back to a control console of the X-ray equipment, and when the rotation degrees of the tube towing wheel reach a degree predefined by an operator, the control console of the X-ray equipment will control the clutch and the SID brake to cut a power source.

11. The cross arm according to claim 1, further comprising at least one photoelectric sensor at a moving path of the tube, wherein the at least one photoelectric sensor is configured to feed back to a control console of the X-ray equipment a message indicating that the tube arrives at a position where the at least one photoelectric sensor is located.

12. An X-ray device comprising:
   a cross arm comprising:
   a guide on the cross arm;
   a tube configured to move along the guide when the cross arm rotates; and
   a linkage device comprising:
   a cross arm rotor configured to rotate the cross arm;
   a rotation actuator configured to allow and disallow the rotation of the cross arm;

a tube towing mechanism configured to move the tube along the guide;

a rotary force drive configured to transmit a power generated by the rotation of the cross arm to the tube towing mechanism; and a rotary force clutch configured to interrupt or to transmit the power transmitted by the rotary force drive to the tube towing mechanism.

13. The X-ray equipment according to claim 12, wherein the cross arm rotor comprises a rotary shaft and a rotary gear configured to rotate about the rotary shaft.

14. The X-ray equipment according to claim 13, wherein the rotary gear is fixed on the cross arm.

15. The X-ray equipment according to claim 13, wherein the rotation actuator comprises:

a brake; and a braking gear on a shaft core of the brake, wherein the braking gear and the rotary gear are engaged with each other.

16. The X-ray equipment according to claim 15, wherein the rotary force drive comprises:

a driving sprocket on the shaft core of the brake; and a driving chain engaged with the driving sprocket.

17. The X-ray equipment according to claim 16, wherein the shaft core of the brake is configured to:

rotate;

drive the braking gear and the driving sprocket to rotate together when the brake is energized; and remain immovable when the brake is de-energized.

18. The X-ray equipment according to claim 16, wherein the rotary force clutch comprises:

a clutch; and a clutch sprocket on a clutch shaft core, wherein the clutch sprocket and the driving chain are engaged with each other.

* * * * *

UNITED STATES PATENT AND TRADEMARK OFFICE
CERTIFICATE OF CORRECTION

| | |
|---|---|
| PATENT NO. | : 9,179,532 B2 |
| APPLICATION NO. | : 13/929275 |
| DATED | : November 3, 2015 |
| INVENTOR(S) | : Ling et al. |

Page 1 of 1

It is certified that error appears in the above-identified patent and that said Letters Patent is hereby corrected as shown below:

On the title page item 73, under "Assignee" in Column 1, Line 2, delete "COMPANY," and insert -- COMPANY --, therefor.

In the specification

In Column 3, Line 65, delete "device 301" and insert -- device 201 --, therefor.

In the claims

In Column 6, Line 24, in Claim 7, delete "comprises a:" and insert -- comprises: --, therefor.

In Column 6, Line 25, in Claim 7, delete "clutch;" and insert -- a clutch; --, therefor.

In Column 6, Line 26, in Claim 7, delete "clutch" and insert -- a clutch --, therefor.

In Column 7, Line 9, in Claim 13, delete "equipment" and insert -- device --, therefor.

In Column 7, Line 12, in Claim 14, delete "equipment" and insert -- device --, therefor.

In Column 7, Line 14, in Claim 15, delete "equipment" and insert -- device --, therefor.

In Column 8, Line 1, in Claim 16, delete "equipment" and insert -- device --, therefor.

In Column 8, Line 5, in Claim 17, delete "equipment" and insert -- device --, therefor.

In Column 8, Line 12, in Claim 18, delete "equipment" and insert -- device --, therefor.

Signed and Sealed this
Fifth Day of July, 2016

Michelle K. Lee
*Director of the United States Patent and Trademark Office*